US011896697B2

(12) United States Patent
Plos et al.

(10) Patent No.: US 11,896,697 B2
(45) Date of Patent: Feb. 13, 2024

(54) COMPOSITION FOR KERATIN FIBERS

(71) Applicant: L'OREAL, Paris (FR)

(72) Inventors: Gregory Plos, Paris (FR); Laetitia Feuillette, Paris (FR); Natsumi Komure, Kanagawa (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/406,610

(22) Filed: May 8, 2019

(65) Prior Publication Data

US 2019/0328639 A1 Oct. 31, 2019

Related U.S. Application Data

(62) Division of application No. 15/572,380, filed as application No. PCT/JP2016/064807 on May 12, 2016, now abandoned.

(30) Foreign Application Priority Data

May 12, 2015 (JP) ................................ 2015-097252
May 12, 2015 (JP) ................................ 2015-097253

(51) Int. Cl.
*A61K 8/44* (2006.01)
*A61K 8/46* (2006.01)
*A61K 8/49* (2006.01)
*A61Q 5/06* (2006.01)
*A61K 8/73* (2006.01)

(52) U.S. Cl.
CPC ................ *A61K 8/44* (2013.01); *A61K 8/466* (2013.01); *A61K 8/4913* (2013.01); *A61K 8/4946* (2013.01); *A61K 8/73* (2013.01); *A61K 8/731* (2013.01); *A61K 8/737* (2013.01); *A61Q 5/06* (2013.01); *A61K 2800/30* (2013.01); *A61K 2800/48* (2013.01)

(58) Field of Classification Search
CPC ... A61Q 5/06; A61K 8/44; A61K 8/73; A61K 8/4913; A61K 8/4946; A61K 2800/30; A61K 2800/48; A61K 8/731; A61K 8/732; A61K 8/737
See application file for complete search history.

(56) References Cited

U.S. PATENT DOCUMENTS

| 2,154,924 A | 4/1939 | Wilson et al. | |
| 2,154,925 A * | 4/1939 | Wilson | A61K 8/49 132/206 |
| 3,778,502 A | 12/1973 | Aubin et al. | |
| 4,459,284 A | 7/1984 | Azuma et al. | |
| 4,610,874 A * | 9/1986 | Matravers | A61K 8/63 424/70.13 |
| 8,343,238 B1 * | 1/2013 | Lopez | A61Q 5/10 8/408 |
| 2002/0034486 A1 * | 3/2002 | Midha | A61K 8/0245 424/70.2 |
| 2010/0183539 A1 * | 7/2010 | Bernhardt | A61K 8/466 424/70.31 |
| 2012/0230935 A1 | 9/2012 | Kim et al. | |
| 2012/0269758 A1 | 10/2012 | Cornwell et al. | |
| 2013/0167861 A1 * | 7/2013 | Lopez | A61K 8/42 132/204 |
| 2015/0297496 A1 * | 10/2015 | Kroon | A61K 8/8182 424/54 |

FOREIGN PATENT DOCUMENTS

| EP | 0129807 A2 * | 1/1885 |
| EP | 0129807 A2 | 1/1985 |
| JP | 57-021311 A | 2/1982 |
| JP | 62-009566 B | 2/1987 |
| JP | H07-291840 A | 11/1995 |
| JP | H09-263521 A | 10/1997 |
| JP | 2000-169344 A | 6/2000 |
| JP | 2006-160669 A | 6/2006 |
| JP | 2006-188441 A | 7/2006 |

(Continued)

OTHER PUBLICATIONS

Heartbeet Kitchen, title: 9 Delicious Ways to Use Collagen in Recipes; date Jul. 18, 2016. Downloaded from https://heartbeetkitchen.com/2016/recipes/dietary/paleo/ways-to-use-collagen-in-recipes/#:~:text=COLLAGEN%20GELATIN%20(only%20beef)%20will,%2C%20cookies%2C%20waffles%2C%20etc. (Year: 2016).*
International Search Report for PCT/JP2016/064807, dated Jul. 22, 2016.
Japanese Office Action for counterpart Application No. 2017-559131, dated Mar. 4, 2019, with translation.
Third Party Observation for counterpart Application No. EP 20160729391.9, dated Oct. 29, 2019.
Korean Office Action for counterpart Application No. 10-2017-7032204, dated Jun. 7, 2019, with English Translation.

(Continued)

*Primary Examiner* — Michael B. Pallay
(74) *Attorney, Agent, or Firm* — THE MARBURY LAW GROUP, PLLC

(57) ABSTRACT

The present invention relates to a composition for reshaping keratin fibers with heat, comprising: (a) at least one organic alkaline agent having a pKa value of from 8.0 to 13.5; and (b) at least one polymeric thickener, (c) at least one organic acidic agent having pKa value of less than 3.5, and/or (d) at least one alkaline agent; wherein the composition has a pH of from 8.0 to 12, preferably from 8.5 to 11.5, and more preferably from 9.0 to 11.0. The composition according to the present invention is preferably a cosmetic composition, for keratin fibers, such as hair, and can be used for a process for reshaping the keratin fibers with heat. The composition according to the present invention can provide the keratin fibers with a sufficient reshaping efficiency such as strong wave intensity of the curled keratin fibers and good usability.

18 Claims, No Drawings

(56) References Cited

FOREIGN PATENT DOCUMENTS

| | | | | |
|---|---|---|---|---|
| JP | 2013-528158 A | 7/2013 | | |
| KR | 10-2008-0092226 A | 10/2008 | | |
| KR | 10-2012-0102270 A | 9/2012 | | |
| WO | 2011/074136 A1 | 6/2011 | | |
| WO | 2011/155076 A1 | 12/2011 | | |
| WO | WO-2012027369 A2 * | 3/2012 | ............... | A61K 8/23 |
| WO | 2012/163594 A2 | 12/2012 | | |
| WO | 2013/092779 A2 | 6/2013 | | |
| WO | 2013/145330 A1 | 10/2013 | | |
| WO | WO-2013145330 A1 * | 10/2013 | ............... | A61Q 5/04 |
| WO | WO 2014071354 A1 * | 5/2014 | | |
| WO | 2014/170336 A1 | 10/2014 | | |
| WO | 2016/102543 A1 | 6/2016 | | |

OTHER PUBLICATIONS

Wikipedia website Ethanolamine, https://en.wikipedia.org/wiki/Ethanolamine, 4 pages (accessed Jul. 9, 2020).

Wikipedia website Triethanolamine, https://en.wikipedia.org/wiki/Triethanolamine, 8 pages (accessed Jul. 9, 2020).

Wikipedia website Morpholine, https://en.wikipedia.org/wiki/Morpholine, 6 pages (accessed Jul. 9, 2020).

Workplace Safety Site, Safety Data Sheet Morpholine, https://anzeninfo.mhlw.go.jp/anzen/gmsds/0995.html, 18 pages (accessed Jul. 9, 2020) Machine translation obtained by machine translator on Dec. 2, 2020.

ChemicalBook website Urea, https://m.chemicalbook.com/ChemicalProductProperty_JP_cb5853861.htm, 17 pages (accessed Jul. 15, 2020).

JP Application No. 2017-559131, Notice of Opposition dated Oct. 14, 2020 (machine translation obtained by machine translator on Dec. 2, 2020).

Wikipedia website [Proteinogenic amino acid], https://en.wikipedia.org/wiki/Proteinogenic_amino_acid (accessed: Nov. 20, 2020).

Notice of Reason for Cancellation for counterpart JP Application No. 2017-559131, dated Dec. 23, 2020.

Machine Translation of Japanese Decision of Opposition for Application No. 2017-559131, dated Jul. 12, 2021.

EP Patent Office, Communication Pursuant to Article 94, pp. 1-3, dated Feb. 20, 2020, European Patent Office, Munich, Germany.†

\* cited by examiner
† cited by third party

COMPOSITION FOR KERATIN FIBERS

CROSS REFERENCE TO RELATED APPLICATIONS

This is a divisional application of U.S. application Ser. No. 15/572,380, filed Nov. 7, 2017, which is a U.S. National Stage Application of PCT/JP2016/064807, filed internationally on May 12, 2016, which claims priority to Japanese Application No. 2015-097252, filed on May 12, 2015, and Japanese Application No. 2015-097253, filed on May 12, 2015, all of which are incorporated by reference herein in their entireties.

TECHNICAL FIELD

The present invention relates to a composition, in particular a cosmetic composition, for keratin fibers such as hair.

BACKGROUND ART

In long-lasting deformation of keratin fibers such as hair, first the disulphide bonds —S—S— of the keratin (cystine) are opened using a composition containing a suitable reducing agent (reduction stage), then the hair thus treated is optionally rinsed, secondly the disulphide bonds are reconstituted by applying, on the keratin fibers previously put under tension (curlers etc.), an oxidizing composition (oxidation stage, also called fixation) so as to finally give the keratin fibers the desired form. This technique thus makes it possible to carry out either waving or straightening of the keratin fibers. For example, JP-B-S62-9566 or U.S. Pat. No. 4,459,284 discloses a standard process for permanent waving or straightening of keratin fibers such as hair in line with the above steps.

The new shape imposed on the keratin fibers by chemical treatment as described above is relatively long-lasting and notably withstands the action of washing with water or shampoo, in contrast to the simple conventional techniques of temporary styling by using foams, styling gels, or lacquers.

Many compositions and processes for the above chemical treatment have been proposed. Generally, they offer good performance on the day of treatment.

However, there are various drawbacks such as follows in the above chemical treatment process that may not be suitable from the view-point of consumer's or hair-dresser's expectations:

Insufficient reshaping efficiency such as weak wave intensity;

Poor usability caused by, for example, dripping of the composition from the hair;

High levels of keratin fiber degradation, especially in repeated applications or in combination with other chemical treatments such as oxidative coloration;

Long processing time; and

Malodor of ammonia or thiol-compounds or sulfur-containing compounds during and after the deformation process.

In particular, sufficient reshaping efficiency and good usability are important. There is indeed a need to improve a deformation process of keratin fibers to provide sufficient reshaping efficiency, such as strong wave intensity of the curled keratin fibers, as well as excellent usability such as no dripping of the composition from the keratin fibers.

DISCLOSURE OF INVENTION

An objective of the present invention is to provide a composition, preferably a cosmetic composition, for keratin fibers, such as hair, which can be used for a process for reshaping the keratin fibers with heat, and can provide the keratin fibers with sufficient reshaping efficiency such as strong wave intensity of the curled keratin fibers and good usability.

The above objective of the present invention can be achieved by a composition, in particular a cosmetic composition, for reshaping keratin fibers, such as hair, with heat comprising:

(a) at least one organic alkaline agent having a pKa value of from 8.0 to 13.5; and
(b) at least one polymeric thickener,
wherein
the composition has a pH of from 8.0 to 12, preferably from 8.5 to 11.5, and more preferably from 9.0 to 11.0.

It is preferable that the (a) organic alkaline agent have a pKa value of from 8.0 to 12.5.

The (a) organic alkaline agent may be selected from the group consisting of amino acids, in particular basic amino acids, such as arginine (Arg), histidine (His) and lysine (Lys), and oligomers of amino acids; monoamines and their derivatives such as monoethanolamine; diamines and their derivatives; polyamines and their derivatives; guanidine and its derivatives; urea and its derivatives; and mixtures thereof.

It is preferable that the (a) organic alkaline agent be selected from basic amino acids, such as arginine (Arg), histidine (His) and lysine (Lys).

The amount of the (a) organic alkaline agent in the composition according to the present invention may be from 0.1 to 25% by weight, preferably from 1 to 20% by weight, and more preferably from 2 to 15% by weight, relative to the total weight of the composition.

The composition according to the present invention may further comprise at least one alkaline agent different from the (a) organic alkaline agent having a pKa value of from 8.0 to 13.5.

The composition according to the present invention may further comprise at least one acid.

It is preferable that the composition according to the present invention does not comprise any ammonia, or comprises less than 1%, preferably less than 0.5%, and more preferably less than 0.1% by weight of ammonia, relative to the total weight of the composition.

The above objective of the present invention can be also achieved by a composition, in particular a cosmetic composition, for reshaping keratin fibers, such as hair, with heat comprising:

(c) at least one organic acidic agent having pKa value of less than 3.5;
(b) at least one polymeric thickener; and
(d) at least one alkaline agent,
wherein
the composition has a pH of from 8 to 12, preferably from 8.5 to 11.5, and more preferably from 9.0 to 11.0; and
the composition is free of ammonia or methionine.

It is preferable that the (c) organic acidic agent have a pKa value of from 1.0 to 3.0.

The (c) organic acidic agent having pKa value of less than 3.5 may be selected from the group consisting of carboxylic acids, aminosulfonic acids such as 2-(cyclohexylamino) ethanesulfonic acid and taurine, amino acids such as glycine, alanine, glutamic acid, aspartic acid, phenyl alanine, β-alanine, isoleucine, leucine, proline, glutamine, serine, threonine, valine, tryptophane, tyrosine, oligomers of amino acids such as glycylglycine, and mixtures thereof, and is preferably selected from the group consisting of glycine, taurine, alanine, proline, 2-(cyclohexylamino)ethanesulfonic acid and mixtures thereof.

The amount of the (c) organic acidic agent having pKa value of less than 3.5 in the composition may be from 0.1 to 25% by weight, preferably from 0.5 to 20% by weight, and more preferably from 1 to 15% by weight, relative to the total weight of the composition.

It is preferable that the (d) alkaline agent is an inorganic alkaline agent.

The (d) alkaline agent may be selected from the group consisting of ammonia; alkaline metal hydroxides; and alkaline earth metal hydroxides, alkaline metal phosphates and or monohydrogenophosphates.

The amount of the (d) alkaline agent in the composition may be from 0.1 to 20% by weight, preferably from 0.2 to 15% by weight, and more preferably from 0.3 to 10% by weight, relative to the total weight of the composition.

It is preferable that the (b) polymeric thickener have at least one sugar unit.

It is preferable that the (b) polymeric thickener be selected from native gums, such as cellulose, guar gum and xanthan gum, and derivatives thereof.

The amount of the (b) polymeric thickener in the composition according to the present invention may be from 0.01 to 10% by weight, preferably from 0.1 to 5% by weight, more preferably from 0.2 to 3% by weight, and even more preferably from 0.5 to 2% by weight, relative to the total weight of the composition.

It is preferable that the viscosity of the composition be 800 mPa·s or more, preferably 1,000 mPa·s or more, and more preferably 1,500 mPa·s or more.

It is preferable that the composition according to the present invention does not comprise any thiol compound, or comprise less than 1%, preferably less than 0.5%, and more preferably less than 0.1% by weight, of a thiol compound relative to the total weight of the composition.

It is preferable that the composition according to the present invention does not comprise any reducing agent or oxidizing agent, or comprises less than 1%, preferably less than 0.5%, and more preferably less than 0.1% by weight of a reducing agent or an oxidizing agent, relative to the total weight of the composition.

The present invention also relates to a reshaping process, in particular permanent waving, for keratin fibers, preferably hair, comprising the steps of:
  applying onto the keratin fibers the composition according to the present invention;
  heating the keratin fibers; and
  optionally rinsing and/or drying the keratin fibers.

It is preferable that the keratin fibers be heated at a temperature of at least 80° C.

The process according to the present invention can be used to deform or reshape keratin fibers, preferably hair, and can provide the keratin fibers with sufficient reshaping efficiency such as good wave intensity of the curled keratin fibers, as well as good usability such as few or no dripping of the composition from the keratin fibers. Also, the process according to the present invention can reduce the damage to the keratin fibers, and can reduce the processing time as compared to a conventional process which uses a reducing agent and an oxidizing agent.

BEST MODE FOR CARRYING OUT THE INVENTION

After diligent research, the inventors have found that the use of a specific combination of (a) at least one organic alkaline agent having a pKa value of from 8.0 to 13.5, (c) at least one organic acidic agent having pKa value of less than 3.5, and/or (d) at least one alkaline agent with (b) at least one polymeric thickener, in a composition for reshaping keratin fibers, in particular hair, which has a pH of from 8.0 to 12, preferably from 8.5 to 11.5 and more preferably from 9.0 to 11.0 can enhance the reshaping efficiency of the keratin fibers, such as strong wave intensity of the curled keratin fibers, and good usability such as no dripping of the composition from the keratin fibers.

Thus, the composition, preferably a cosmetic composition, for reshaping keratin fibers, preferably hair, with heat according to the present invention comprises:
  (a) at least one organic alkaline agent having a pKa value of from 8.0 to 13.5; and
  (b) at least one polymeric thickener,
  wherein
  the composition has a pH of from 8.0 to 12, preferably from 8.5 to 11.5, and more preferably from 9.0 to 11.0.

Also, the composition, preferably a cosmetic composition, for reshaping keratin fibers, preferably hair, with heat according to the present invention comprises:
  (c) at least one organic acidic agent having pKa value of less than 3.5;
  (b) at least one polymeric thickener; and
  (d) at least one alkaline agent,
  wherein
  the composition has a pH of from 8 to 12, preferably from 8.5 to 11.5, and more preferably from 9.0 to 11.0; and
  the composition is free of ammonia or methionine.

Hereafter, the composition according to the present invention and the process according to the present invention will each be described in a detailed manner.

[Composition]

The composition for reshaping keratin fibers with heat according to the present invention comprises:
  (a) at least one organic alkaline agent having a pKa value of from 8.0 to 13.5; and
  (b) at least one polymeric thickener,
  wherein
  the composition has a pH of from 8.0 to 12, preferably from 8.5 to 11.5, and more preferably from 9.0 to 11.0.

Also, the composition for reshaping keratin fibers with heat according to the present invention comprises:
  (c) at least one organic acidic agent having pKa value of less than 3.5;
  (b) at least one polymeric thickener; and
  (d) at least one alkaline agent,
  wherein
  the composition has a pH of from 8 to 12, preferably from 8.5 to 11.5, and more preferably from 9.0 to 11.0; and
  the composition is free of ammonia or methionine.

Both of these compositions according to present invention comprises the (b) at least one polymeric thickener.

It is preferable that the composition according to the present invention be a cosmetic composition, in particular for reshaping keratin fibers. It is preferable that the keratin fibers be hair.

The term "free of ammonia or methionine" means that the composition according to the present invention does not include a substantial amount of ammonia or methionine. Preferably the composition according to the present invention includes 1% by weight or less, more preferably 0.5% by weight or less, and even more preferably 0.1% by weight or less of ammonia or methionine, in particular no ammonia or methionine.

(Organic Alkaline Agent Having pKa Value of from 8.0 to 13.5)

The composition according to the present invention may comprise (a) at least one organic alkaline agent having a pKa value of from 8.0 to 13.5. Two or more (a) organic alkaline agent having a pKa value of from 8.0 to 13.5 may be used in combination. Thus, a single type of organic alkaline agent having a pKa value of from 8.0 to 13.5 or a combination of different types of organic alkaline agent having a pKa value of from 8.0 to 13.5 may be used.

The pKa value may be measured at 25° C.

The (a) organic alkaline agent having a pKa value of from 8.0 to 13.5 has at least one pKa value from 8.0 to 13.5, and may have two or more pKa values. If the (a) organic alkaline agent has two or more pKa values, at least one of the pKa values must be in a range from 8.0 to 13.5.

One should recall that the term "organic" means that the alkaline agent has at least one carbon atom in its chemical structure.

It is preferable that the (a) organic alkaline agent having a pKa value of from 8.0 to 13.5 be non-volatile. One should recall that the term "non-volatile" means that the alkaline agent has a vapor pressure generally lower than 0.02 mmHg (2.66 Pa) at room temperature.

The (a) organic alkaline agent having a pKa value of from 8.0 to 13.5 may be selected from the group consisting of amino acids and oligomers of amino acids; monoamines and their derivatives such as monoethanolamine; diamines and their derivatives; polyamines and their derivatives; guanidine and its derivatives; urea and its derivatives; and mixtures thereof.

The amino acids that may be used are of natural or synthetic origin, in their L, D or racemic form, and comprise at least one acid function chosen particularly from carboxylic acid, sulphonic acid, phosphonic acid or phosphoric acid functions. It is preferable that the amino acids which may be used according to the present invention comprise at least one amine group and at least one carboxylic acid group. The amino acids may be in neutral or ionic form.

The amino acids that may be used according to the present invention may be α-amino acids, β-amino acids, or γ-amino acids. Preferably, the amino acids used in the present invention are α-amino acids, i.e., they comprise an amine function and an acid function at the same carbon atom.

The α-amino acids may be represented by the following formula (I):

$$R—CH—COOH \atop | \atop N(H)_p \qquad (I)$$

in which:
when p=2, R represents a hydrogen atom, an aliphatic group optionally containing one or several nitrogen atoms, a heterocyclic portion, or an aromatic group, or
when p=1, R can form a heterocycle with the nitrogen atom of $—N(H)_p$. This heterocycle is preferably a saturated 5-membered ring, optionally substituted with one or more $C_1$-$C_4$ alkyl or hydroxyl groups.

Preferably, the aliphatic group is a linear or branched $C_1$-$C_4$ alkyl group; a linear or branched $C_1$-$C_4$ hydroxyalkyl group; a linear or branched $C_1$-$C_4$ aminoalkyl group; a linear or branched ($C_1$-$C_4$ alkyl)thio($C_1$-$C_4$)alkyl group; a linear or branched $C_2$-$C_4$ carboxyalkyl group; a linear or branched ureidoalkyl group, a linear or branched guanidinoalkyl group, a linear or branched imidazoloalkyl group or a linear or branched indolylalkyl group, the alkyl portions of these last four groups comprising from one to four carbon atoms.

Preferably, the aromatic group is a $C_6$ aryl or $C_7$-$C_{10}$ aralkyl group, the aromatic nucleus optionally being substituted with one or more $C_1$-$C_4$ alkyl or hydroxyl groups.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, threonine, tryptophan, tyrosine and valine.

The (a) organic alkaline agent having a pKa value of from 8.0 to 13.5 may have two or more carboxylic acids, such as aspartic acid and glutamic acid.

Preferably, the (a) organic alkaline agent may be basic amino acids, comprising an additional amine function optionally included in a ring or in a ureido function.

Such basic amino acids may be preferably chosen from those corresponding to formula (II) below:

$$R—CH_2—CH{\overset{NH_2}{\underset{CO_2H}{\diagup\kern-0.5em\diagdown}}} \qquad (II)$$

in which R denotes a group chosen from:

—(imidazole ring with NH)—    —$(CH_2)_2NH_2$    —$(CH_2)_2NH—\underset{\overset{\|}{NH}}{C}—NH_2$

—$(CH_2)_3NH_2$    —$(CH_2)_2NHCONH_2$

The compounds corresponding to formula (II) may be histidine, lysine, arginine, ornithine and citrulline. It may be preferable that the (a) organic alkaline agent having a pKa value of from 8.0 to 13.5 be selected from basic amino acids such as arginine (Arg), histidine (His) and lysine (Lys).

As examples of the monoamines, mention may be made of alkanolamines such as mono-, di- and tri-ethanolamine, comprising 1 to 3 hydroxyalkyl($C_1$-$C_4$) groups. Particularly, alkanolamines may be selected from monoethanolamine, diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino)methane.

The diamines may be described in the structure (III) below:

$$\overset{R_a}{\underset{R_c}{\diagdown\kern-0.5em\diagup}}N—W—N\overset{R_b}{\underset{R_d}{\diagup\kern-0.5em\diagdown}} \qquad (III)$$

wherein W denotes an alkylene such as propylene optionally substituted by a hydroxyl or a $C_1$-$C_4$ alkyl radical, and $R_a$, $R_b$, $R_c$ and $R_d$ independently denote a hydrogen atom, an alkyl radical or a $C_1$-$C_4$ hydroxyalkyl radical, which may be exemplified by 1,3-propanediamine and derivatives thereof.

It is preferable that the (a) organic alkaline agent having a pKa value of from 8.0 to 11, more preferably from 8.5 to 10.5, and even more preferably from 9.0 to 10.0.

It is preferable that the (a) organic alkaline agent having a pKa value of from 8.0 to 13.5 be selected from the group consisting of arginine, histidine, lysine and mixtures thereof.

The amount of the (a) organic alkaline agent in the composition according to the present invention may be from 0.1 to 25% by weight, preferably from 1 to 20% by weight, and more preferably from 2 to 15% by weight, relative to the total weight of the composition.

(Organic Acidic Agent Having pKa Value of Less than 3.5)

The composition according to the present invention may comprises (c) at least one organic acidic agent having pKa value of less than 3.5. Two or more (c) organic acidic agent having pKa value of less than 3.5 may be used in combination. Thus, a single type of organic acidic agent having pKa value of less than 3.5 or a combination of different types of organic acidic agent having pKa value of less than 3.5 may be used.

The pKa value may be measured at 25° C.

The (c) organic acidic agent having a pKa value of less than 3.5 has at least one pKa value less than 3.5, and may have two or more pKa values. If the (c) organic acidic agent has two or more pKa values, at least one of the pKa values must be in a range less than 3.5.

One should recall that the term "organic" means that the acidic agent has at least one carbon atom in its chemical structure.

It is preferable that the (c) organic acidic agent having pKa value of less than 3.5 be non-volatile. One should recall that the term "non-volatile" means that the acidic agent has a vapor pressure generally lower than 0.02 mmHg (2.66 Pa) at room temperature.

The (c) organic acidic agent having pKa value of less than 3.5 may be selected from the group consisting of carboxylic acids, aminosulfonic acids, amino acids such as glycine, alanine, glutamic acid, aspartic acid, phenyl alanine, β-alanine, isoleucine, leucine, proline, glutamine, serine, threonine, valine, tryptophane, tyrosine, oligomers of amino acids such as glycylglycine, and mixtures thereof.

The carboxylic acids having pKa value of less than 3.5 may be selected from the group consisting of oxalic acid, malonic acid, maleic acid, salicylic acid, phthalic acid, and mixtures thereof.

The aminosulfonic acid having pKa value of less than 3.5 may be selected from the group consisting of taurine, 2-(cyclohexylamino)ethanesulfonic acid, and mixtures thereof.

It is preferable that the (c) organic acidic agent having pKa value of less than 3.5 be selected from taurine, 2-(cyclohexylamino)ethanesulfonic acid, amino acids having a pKa value of less than 3.5, and mixtures thereof.

The amino acids that may be used according to the present invention may be α-amino acids, β-amino acids, or γ-amino acids. Preferably, the amino acids used in the present invention are α-amino acids, i.e., they comprise an amine function and an acid function at the same carbon atom.

The α-amino acids may be represented by the following formula (I):

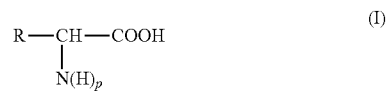

in which:
when p=2, R represents a hydrogen atom, an aliphatic group optionally containing one or several nitrogen atoms, a heterocyclic portion, or an aromatic group, or
when p=1, R can form a heterocycle with the nitrogen atom of —N(H)$_p$. This heterocycle is preferably a saturated 5-membered ring, optionally substituted with one or more $C_1$-$C_4$ alkyl or hydroxyl groups.

Preferably, the aliphatic group is a linear or branched $C_1$-$C_4$ alkyl group; a linear or branched $C_1$-$C_4$ hydroxyalkyl group; a linear or branched $C_1$-$C_4$ aminoalkyl group; a linear or branched ($C_1$-$C_4$ alkyl)thio($C_1$-$C_4$)alkyl group; a linear or branched $C_2$-$C_4$ carboxyalkyl group; a linear or branched ureidoalkyl group, a linear or branched guanidinoalkyl group, a linear or branched imidazoloalkyl group or a linear or branched indolylalkyl group, the alkyl portions of these last four groups comprising from one to four carbon atoms.

Preferably, the aromatic group is a $C_6$ aryl or $C_7$-$C_{10}$ aralkyl group, the aromatic nucleus optionally being substituted with one or more $C_1$-$C_4$ alkyl or hydroxyl groups.

It is preferable that the amino acids be selected from acidic amino acids and neutral amino acids. The term "neutral amino acids" is intended to mean amino acids which have a pH, at ambient temperature (25° C.), in water of inclusively between 5 and 7. The term "acidic amino acids" is intended to mean amino acids which have a pH, at ambient temperature, in water of less than 5.

As acidic amino acids and neutral amino acids that may be used in the present invention, mention may be made especially of aspartic acid, glutamic acid, alanine, asparagine, carnitine, glutamine, glycine, isoleucine, leucine, phenylalanine, proline, serine, threonine, tryptophan, tyrosine and valine.

The (c) organic acidic agent having pKa value of less than 3.5 may have two or more carboxylic acids, such as aspartic acid and glutamic acid.

It is preferable that the (c) organic acidic agent have a pKa value of from 0.5 to 3.5, more preferably from 1.0 to 3.0, and even more preferably from 1.5 to 2.8.

It is preferable that the (c) organic acidic agent having pKa value of less than 3.5 be selected from the group consisting of glycine, taurine, alanine, proline, 2-(cyclohexylamino)ethanesulfonic acid and mixtures thereof.

The amount of the (c) organic acidic agent having pKa value of less than 3.5 in the composition according to the present invention may be from 0.1 to 25% by weight, preferably from 0.5 to 20% by weight, and more preferably from 1 to 15% by weight, relative to the total weight of the composition.

(Alkaline Agent)

The composition according to the present invention may comprise (d) at least one alkaline agent. Two or more (d) alkaline agents may be used in combination. Thus, a single type of alkaline agent or a combination of different types of alkaline agents may be used.

The (d) alkaline agent is different from the (c) organic acidic agent having pKa value of less than 3.5 or different from the (a) organic alkaline agent having a pKa value of from 8.0 to 13.5.

The (d) alkaline agent may be an inorganic alkaline agent. It is preferable that the (d) alkaline agent be non-volatile. It is preferable that the inorganic alkaline agent be selected from the group consisting of alkaline metal hydroxides; alkaline earth metal hydroxides; alkaline metal phosphates and monohydrogenophosphates such as sodium phosphate or sodium monohydrogenophosphate.

As examples of the inorganic alkaline metal hydroxides, mention may be made of sodium hydroxide, lithium hydroxide and potassium hydroxide. As examples of the alkaline earth metal hydroxides, mention may be made of calcium hydroxide and magnesium hydroxide. As the inorganic alkaline agent, sodium hydroxide is preferable.

The (d) alkaline agent(s) may be used in a total amount of from 0.1 to 20% by weight, preferably from 0.2 to 15% by weight, more preferably from 0.3 to 10% by weight, and even more preferably from 0.5 to 5% by weight, relative to the total weight of the composition, depending on their solubility.

(Polymeric Thickener)

The composition according to the present invention comprises (b) at least one polymeric thickener. Two or more (b) polymeric thickeners may be used in combination. Thus, a single type of polymeric thickener or a combination of different types of polymeric thickeners may be used.

As used herein, "polymeric thickener" means a polymer which, when added at 1 wt % to an aqueous medium or aqueous-alcoholic solution at 30% of ethanol, and at pH=7 or to an oil chosen from liquid paraffin, isopropyl myristate and cyclopentadimethylsiloxane, gives a viscosity of at least 100 cP, such as at least 500 cP, at 25° C. and at a shear rate of is-1. This viscosity can be measured using a rotary viscometer (Vismetron VS-A1: Rotor No. 3, 12 rpm, High, 30 seconds) at 25° C.

It is preferable that the (b) polymeric thickener can cause thickening of an aqueous medium.

The (b) polymeric thickener can be an ionic or non-ionic, associative or non-associative polymer. As used herein, the non-associative polymeric thickeners are polymeric thickeners not containing a $C_{10}$-$C_{30}$ fatty chain.

As the (b) polymeric thickener, non-limiting mention can be made of polymeric thickeners with at least one sugar unit. The "sugar unit" means, as used herein, a unit derived from a carbohydrate of formula $C_n(H_2O)_{n-1}$ or $(CH_2O)_n$, which can optionally be modified by substitution, and/or by oxidation and/or by dehydration.

The sugar units of the (b) polymeric thickeners may be, for example, derived from the following sugars: glucose, galactose, arabinose, rhamnose, mannose, xylose, fucose, anhydrogalactose, galacturonic acid, glucuronic acid, mannuronic acid, galactose sulphate, and/or anhydrogalactose sulphate.

Examples of the (b) polymeric thickeners include: native gums such as:
a) exudates from trees or shrubs including but not being limited to: gum arabic (branched polymer of galactose, arabinose, rhamnose and glucuronic acid), ghatti gum (polymer derived from arabinose, galactose, mannose, xylose and glucuronic acid), karaya gum (polymer derived from galacturonic acid, galactose, rhamnose and glucuronic acid), gum tragacanth (polymer of galacturonic acid, galactose, fucose, xylose and arabinose);
b) gums derived from algae, including without being limited to: agar (polymer derived from galactose and anhydrogalactose), alginates (polymers of mannuronic acid and glucuronic acid), carrageenans and furcelleranes (polymers of galactose sulphate and anhydrogalactose sulphate);
c) gums derived from seeds or tubers, including without being limited to: guar gum (polymer of mannose and galactose), carob gum (polymer of mannose and galactose), fenugreek gum (polymer of mannose and galactose), tamarind gum (polymer of galactose, xylose and glucose), konjac gum (polymer of glucose and mannose);
d) microbial gums, including without being limited to: xanthan gum (polymer of glucose, mannose acetate, mannose/pyruvic acid and glucuronic acid), gellan gum (polymer of partially acylated glucose, rhamnose and glucuronic acid), scleroglucan gum (polymer of glucose); and
e) plant extracts, including without being limited to: cellulose (polymer of glucose), starch (polymer of glucose).

These polymers can be modified physically or chemically. As a physical treatment, non-limiting mention can be made of thermal treatment.

As chemical treatments, non-limiting mention can be made of the reactions of esterification, etherification, amidation, and oxidation. These treatments can give polymers which can, for example, be non-ionic, anionic or amphoteric. For example, these chemical or physical treatments may be applied to guar gums, carob gums, starches and celluloses.

The non-ionic guar gums usable according to the disclosure can be modified by $C_1$-$C_6$ hydroxyalkyl groups. Among the hydroxyalkyl groups, non-limiting mention can be made of the hydroxymethyl, hydroxyethyl, hydroxypropyl and hydroxybutyl groups. These guar gums may be well known from the art and can for example be prepared by reacting the oxides of corresponding alkenes, for example propylene oxides, with guar gum to obtain a guar gum modified by hydroxypropyl groups. The rate of hydroxyalkylation, for example, can vary from 0.4 to 1.2 and correspond to the number of molecules of alkylene oxide consumed by the number of free hydroxyl functions present on the guar gum. The non-ionic guar gums optionally modified by hydroxyalkyl groups are for example sold under the trade names JAGUAR HP8, JAGUAR HP60 and JAGUAR HP120 by the company RHODIA CHIMIE.

The starch molecules which may be used in the present invention can have, as botanical origin, cereals or tubers. Thus, the starches are chosen for example from maize starch, rice starch, manioc starch, barley starch, potato starch, wheat starch, sorghum starch, and pea starch. The starches can be modified chemically or physically: for example, by at least one of the reactions chosen from pregelatinization, oxidation, crosslinking, esterification, etherification, amidation, and thermal treatments. For example, these reactions can be carried out as follows:
pregelatinization, by causing the starch grains to burst (for example drying and cooking in a drying drum);
oxidation by strong oxidizing agents leading to the introduction of carboxyl groups in the starch molecule and to depolymerization of the starch molecule (for example by treating an aqueous solution of starch with sodium hypochlorite);
crosslinking by functional agents that are able to react with the hydroxyl groups of the starch molecules, which will thus be joined together (for example with glyceryl and/or phosphate groups); and
esterification in alkaline medium for the grafting of functional groups, such as $C_1$-$C_6$ acyl (acetyl), $C_1$-$C_6$ hydroxyalkyls (hydroxyethyl, hydroxypropyl), carboxymethyl, or octenylsuccinic.

For example, by crosslinking with phosphorus-containing compounds, monostarch phosphates (of the type St-O—PO—(OX)$_2$), distarch phosphates (of the type St-O—PO—(OX)—O-St) or even tristarch phosphates (of the type St-O—PO—(O-St)$_2$) or mixtures thereof (St signifying starch) can be obtained. In the above formulae, X denotes, for example, alkali metals (for example sodium or potassium), alkaline-earth metals (for example calcium or magnesium), salts of ammonia, salts of amines such as those of monoethanolamine, diethanolamine, triethanolamine, and amino-3-propanediol-1,2, or ammonium salts derived from basic amino acids such as lysine, arginine, sarcosine, ornithine, or citrulline.

The phosphorus-containing compounds can be, for example, sodium tripolyphosphate, sodium orthophosphate, phosphorus oxychloride or sodium trimetaphosphate.

In some embodiments, distarch phosphates or compounds rich in distarch phosphate can be used, such as the product offered under the reference names PREJEL VA-70-T AGGL (phosphate of gelatinized, hydroxypropylated manioc distarch) or PREJEL TK1 (phosphate of gelatinized manioc distarch) or PREJEL 200 (phosphate of gelatinized acetylated manioc distarch) by the company AVEBE or STRUCTURE ZEA from NATIONAL STARCH (phosphate of gelatinized maize distarch).

In some embodiments, the starch is a starch that has undergone at least one chemical modification, such as at least one esterification.

According to the present invention, it is also possible to use amphoteric starches, comprising at least one anionic group and at least one cationic group. The at least one anionic and at least one cationic group can be bound to the same reactive site of the starch molecule or to different reactive sites; for example, they can be bound to the same reactive site. The at least one anionic group can be of the carboxyl, phosphate or sulphate type, for example carboxyl. The at least one cationic group can be of the primary, secondary, tertiary or quaternary amine type.

The amphoteric starches may be chosen from, for example, the compounds of the following formulae:

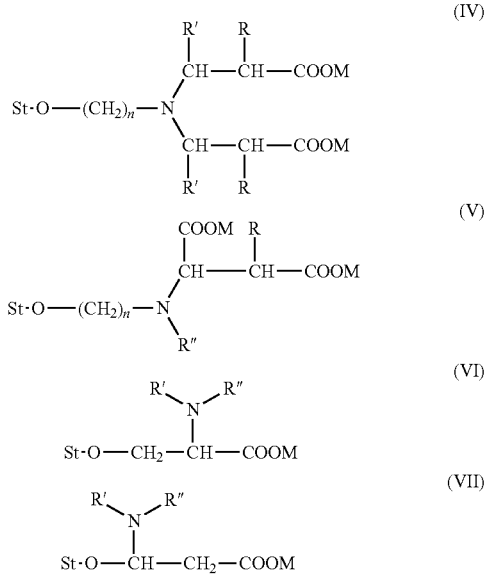

wherein
St-O represents a starch molecule,
R, which can be identical or different, represents a hydrogen atom or a methyl radical,
R', which can be identical or different, represents a hydrogen atom, a methyl radical or a —COOH group,
n is an integer equal to 2 or 3,
M, identical or different, denotes a hydrogen atom, an alkali or alkaline-earth metal such as Na, K, L$_1$, NH$_4$, a quaternary ammonium or an organic amine,
R" represents a hydrogen atom or an alkyl radical having from 1 to 18 carbon atoms.

These compounds are, for example, described in U.S. Pat. Nos. 5,455,340 and 4,017,460, which are incorporated herein by reference.

The starch molecules can be obtained from all vegetable sources of starch, such as maize, potato, oats, rice, tapioca, sorghum, barley or wheat. The hydrolysates of the aforementioned starches can also be used. The starch is, for example, obtained from potato.

In some embodiments, the starches of formulae (V) or (VI) can be used. For example, the starches modified by 2-chloroethyl aminodipropionic acid can be used, i.e. the starches of formula (V) or (VI) in which R, R', R" and M represent a hydrogen atom and n is equal to 2. One exemplary amphoteric starch is a starch chloroethylamidodipropionate.

As stated previously, the derivatives of celluloses can for example be anionic, amphoteric or non-ionic.

Among these derivatives, non-limiting mention can be made of the ethers of celluloses, the esters of celluloses and the ester-ethers of celluloses.

The esters of celluloses include but are not limited to the inorganic esters of cellulose (cellulose nitrates, sulphates or phosphates etc.), the organic esters of cellulose (cellulose monoacetates, triacetates, amidopropionates, acetatebutyrates, acetatepropionates or acetatetrimellitates etc.) and the organic/inorganic mixed esters of cellulose such as cellulose acetatebutyratesulphates and cellulose acetatepropionatesulphates. Among the ester-ethers of cellulose, non-limiting mention can be made of the hydroxypropylmethylcellulose phthalates and the ethylcellulose sulphates.

Among the non-ionic cellulose ethers, non-limiting mention can be made of the alkylcelluloses such as the methylcelluloses and the ethylcelluloses (for example Ethocel standard 100 Premium from DOW CHEMICAL); the hydroxyalkylcelluloses such as the hydroxymethylcelluloses and the hydroxyethylcelluloses (for example Natrosol 250 HHR offered by AQUALON) and the hydroxypropylcelluloses (for example Klucel E F from AQUALON); the mixed hydroxyalkyl-alkylcelluloses such as the hydroxypropyl-methylcelluloses (for example Methocel E4M from DOW CHEMICAL), the hydroxyethyl-methylcelluloses, the hydroxyethyl-ethylcelluloses (for example Bermocoll E 481 FQ from AKZO NOBEL) and the hydroxybutyl-methylcelluloses.

Among the anionic cellulose ethers, non-limiting mention can be made of the carboxyalkylcelluloses and their salts. As examples, mention can be made of the carboxymethylcelluloses, the carboxymethylmethylcelluloses (for example Blanose 7M from the company AQUALON) and the carboxymethylhydroxyethylcelluloses and their sodium salts.

Among the non-associative polymeric thickeners without sugar units that can be used as the (b) polymeric thickener, non-limiting mention can be made of the crosslinked homopolymers or copolymers of acrylic or methacrylic acid, crosslinked homopolymers of 2-acrylamido-2-methyl-propane sulphonic acid and their crosslinked acrylamide copolymers, the homopolymers of ammonium acrylate or the copolymers of ammonium acrylate and acrylamide, alone or mixed.

The associative polymer that may be used according to the invention is water-soluble polymers that are capable, in an aqueous medium, of reversibly combining with each other or with other molecules.

Their chemical structure comprises hydrophilic zones, and hydrophobic zones characterized by at least one fatty chain comprising preferably from 10 to 30 carbon atoms.

The associative polymer that may be used according to the invention may be of anionic, cationic, amphoteric or non-ionic type, such as the polymers sold under the names Pemulen TR1 or TR2 by the company Goodrich (INCI: Acrylates/C10-30 Alkyl Acrylate Crosspolymer), Salcare SC90 by the company Ciba, Aculyn 22, 28, 33, 44 or 46 by the company Röhm & Haas and Elfacos T210 and T212 by the company Akzo.

The polymeric thickener or thickeners for aqueous phase of the disclosure can be chosen from the associative and non-associative polymers with sugar units, the associative and non-associative acrylic and methacrylic anionic polymers, and the associative and non-associative polyurethanes.

It is preferable hat the (b) polymeric thickener be selected from native gums, such as cellulose, guar gum and xanthan gum, and derivatives thereof.

The amount of the (b) polymeric thickener in the composition according to the present invention may be from 0.01 to 10% by weight, preferably from 0.1 to 5% by weight, more preferably from 0.2 to 3% by weight, and even more preferably from 0.5 to 2% by weight, relative to the total weight of the composition.

(Acid)

The composition according to the present invention may comprise at least one acid. The acid is different from the (a) organic alkaline agent having a pKa value of from 8.0 to 13.5 or different from the (c) organic acidic agent having a pKa value of less than 3.5. Two or more acids may be used in combination. Thus, a single type of acid or a combination of different types of acids may be used.

The acid may be used to adjust the pH of the composition according to the present invention.

As the acid, mention may be made of any inorganic or organic acids which are commonly used in cosmetic products such as citric acid, lactic acid, sulfuric acid, phosphoric acid or hydrochloric acid (HCl). HCl is preferable.

The acid(s) may be used in a total amount of from 0.1 to 15% by weight, preferably from 0.2 to 10% by weight, more preferably from 0.3 to 5% by weight, relative to the total weight of the composition, depending on their solubility.

(Other Ingredients)

The composition of the invention may be aqueous or anhydrous. It is preferably aqueous and then comprises water at a concentration ranging from 10% to 99%, better still from 30% to 99% and even better still from 50% to 98% by weight relative to the total weight of the composition.

The composition may in particular comprise one or more organic solvents that are in particular water-soluble, such as $C_1$-$C_7$ alcohols; mention may in particular be made of $C_1$-$C_7$ aliphatic monoalcohols, for instance ethanol, or $C_6$-$C_7$ aromatic monoalcohols, which may be used alone or as a mixture with water.

The composition used in the process of the invention may also comprise at least one customary cosmetic ingredient, chosen in particular from; oils; solid fatty substances and in particular $C_8$-$C_{40}$ esters, $C_8$-$C_{40}$ acids; $C_8$-$C_{40}$ alcohols, sunscreens; moisturizers; antidandruff agents; antioxidants; chelating agents; nacreous agents and opacifiers; plasticizers or coalescers; fillers; emulsifiers; polymers, in particular conditioning polymers, such as cationic polymers; fragrances; silanes; crosslinking agents; surfactants including anionic, cationic, amphoteric and nonionic surfactants. The composition can, of course, comprise several cosmetic ingredients appearing in the above list.

Depending on their nature and the purpose of the composition, the normal cosmetic ingredients can be present in normal amounts which can be easily determined by those skilled in the art and which can be, for each ingredient, between 0.01% and 80% by weight. Those skilled in the art will take care to choose the ingredients included in the composition, and also the amounts thereof, such that they do not harm the properties of the compositions of the present invention.

The compositions used in the process according to the invention may be in any of the formulation forms conventionally used, and in particular in the form of an aqueous, alcoholic or aqueous-alcoholic, or oily solution or suspension; a solution or a dispersion of the lotion or serum type; an emulsion, in particular of liquid or semi-liquid consistency, of the O/W, W/O or multiple type; a suspension or emulsion of soft consistency of cream (O/W) or (W/O) type; an aqueous or anhydrous gel, or any other cosmetic form.

(pH)

The composition according to the present invention has a pH of from 8.0 to 12, preferably from 8.5 to 11.5, and more preferably from 9.0 to 11.0, which is measured at 25° C.

Thus, the composition according to the present invention is not anhydrous.

(Viscosity)

It is preferable that the composition according to the present invention have a viscosity of 800 mPa·s or more, more preferably 1,000 mPa·s or more, and even more preferably 1,500 mPa·s or more. The viscosity can be measured with a rotatory viscometer (Vismetron VS-A1: Rotor No. 3, 12 rpm, High, 30 seconds) at 25° C.

It is also preferable that the composition according to the present invention have a viscosity of 20,000 mPa·s or less, more preferably 15,000 mPa·s or less, and even more preferably 10,000 mPa·s or less.

It may be preferable that the composition according to the present invention have a viscosity of from 800 to 8,000 mPa·s, more preferably from 1,000 to 6,000 mPa·s, even more preferably from 1,500 to 4,000 mPa·s, and in particular from 2,000 to 3,000 mPa·s.

(Ammonia and Thiol Compound)

It is preferable that the composition according to the present invention be free of ammonia or a thiol compound. The term "free of ammonia or a thiol compound" means that the composition according to the present invention does not include a substantial amount of ammonia or a thiol compound. Preferably the composition according to the present invention includes 1% by weight or less, more preferably 0.5% by weight or less, and even more preferably 0.1% by weight or less of ammonia or a thiol compound, in particular no ammonia or the thiol compound.

Due to the very small amount or the absence of ammonia and/or thiol compound, malodor during the use of the composition of the present invention is reduced or prevented.

The thiol compound here means a compound which has at least one thiol (—SH) group.

The thiol compound may be a reducing agent. The thiol reducing agent may be chosen from the group consisting of thioglycolic acid and derivatives thereof, in particular esters thereof such as glycerol or glycol monothioglycolate; thiolactic acid and derivatives thereof, in particular esters thereof such as glycerol monothiolactate; 3-mercaptopropionic acid and derivatives thereof, in particular esters thereof such as glycerol 3-mercaptopropionate and ethyleneglycol 3-mercaptopropionate; cysteamine and derivatives thereof, in particular $C_1$-$C_4$ acyl derivatives thereof such as N-acetylcysteamine and N-propionylcysteamine; mono-thioglycerol and derivatives thereof, in particular esters; cysteine and derivatives thereof, in particular esters such as N-acetylcysteine, N-alkanoylcysteine and cysteine alkyl esters; thioglycerine and derivatives thereof, in particular s-alkyl derivatives, and salts thereof.

As the above salts, mention may be made of, for example, ammonium salts; primary-, secondary- or tertiary-amine salts; alkaline metal salts; and, alkaline earth metal salts. As the primary-, secondary- or tertiary-amine, for example, monoethanolamine, di-isopropanolamine or triethanolamine, respectively, may be mentioned.

Other examples of the thiol reducing agent include, but are not limited to, sugar N-mercapto alkyl amides such as N-(mercapto-2-ethyl)glucoamide, β-mercaptopropionic acid and derivatives thereof thiomalic acid; pantheteine; N-(mercaptoalkyl)ω-hydroxyalkyl amides such as those described in European Patent Application No. 0 354 835 and N-mono- or N,N-dialkylmercapto 4-butyramides such as those described in European Patent Application No. 0 368 763; aminomercaptoalkyl amides such as those described in European Patent Application No. 0 432 000 and alkylaminomercaptoalkylamides such as those described in European Patent Application No. 0 514 282; (2/3) hydroxy-2 propyl thioglycolate; and the hydroxy-2 methyl-1 ethyl thioglycolate-based mixture (67/33) described in French Patent Application No. 2 679 448.

(Reducing Agent and Oxidizing Agent)

The composition according to the present invention may comprise a reducing agent; however, it is preferable that the composition according to the present invention comprises a reduced amount of a reducing agent or an oxidizing agent, preferably free of a reducing agent or an oxidizing agent.

The term "free of a reducing agent or an oxidizing agent" means that the composition according to the present invention does not include a substantial amount of a reducing agent or an oxidizing agent. Preferably the composition according to the present invention includes 1% by weight or less, more preferably 0.5% by weight or less, and even more preferably 0.1% by weight or less of a reducing agent or an oxidizing agent, in particular no reducing agent or no oxidizing agent.

The reducing agent may be a thiol reducing agent or a non-thiol reducing agent. The thio reducing agent is as described above.

The non-thiol reducing agent here means a reducing agent with no thiol group. The non-thiol reducing agent may be chosen from the group consisting of sulfites, bisulfites, sulfinates, phosphines, sugars, reductones and hydrides. The non-thiol reducing agent may be selected from ammonium sulfites and bisulfites as well as metal sulfites and bisulfites, more preferably alkali metal or alkali earth metal sulfites and bisulfites, and more preferably sodium sulfites and bisulfites.

The oxidizing agent may be chosen from hydrogen peroxide, alkali metal bromates, ferricyanides peroxygenated salts, and compounds capable of producing hydrogen peroxide by hydrolysis. For example, the oxidizing agent can be chosen from aqueous hydrogen peroxide solution, urea peroxide, alkali metal bromates and persalts such as perborates and persulphates

[Process]

The composition according to the present invention may be intended for a process for reshaping keratin fibers with heat.

The present invention also relates to a reshaping process, in particular permanent waving, for keratin fibers, preferably the hair.

The reshaping process according to the present invention can be performed by:
  applying onto the keratin fibers the composition according to the present invention;
  heating the keratin fibers; and
  optionally rinsing and/or drying the keratin fibers.

According to the process, the composition according to the present invention is applied to keratin fibers such as hair. The application of the composition may be performed by any means, such as a brush and a comb. It may be possible that the keratin fibers are left as they are for a certain amount of time, if necessary.

The composition which has just been described can be applied to dry or wet hair, preferably to dry hair.

The bath ratio of the applied composition may range from 0.1 to 10, more particularly from 0.2 to 5 and preferably between 0.5 and 3. The term "bath ratio" is intended to mean the ratio between the total weight of the applied composition and the total weight of keratin fibres to be treated.

Before or after the application of the composition according to the present invention to the keratin fibers, the keratin fibers may be subjected to mechanical tension for reshaping or deformation. The mechanical tension can be applied to the keratin fibers by any means to reshape or deform the keratin fibers to an intended shape. For example, the mechanical tension may be provided by at least one reshaping means selected from the group consisting of a curler, a roller, a clip, a plate and an iron. The reshaping means may comprise at least one heater. If the keratin fibers are rolled around a curler, this rolling-up may be performed on the entire length of the keratin fibers or, for example, on half the length of the keratin fibers. Depending on, for example, the desired hairstyle shape and amount of curls, the rolling-up may be performed with more or less thick locks. Optionally, the keratin fibers may be placed in an occlusive or closed space. The occlusive space may be formed by at least one coating means. For example, a coating means is wound around keratin fibers to form the occlusive or closed space. A plurality of coating means may be used. The coating means may be rigid or flexible.

The coating means may comprise at least one member selected from the group consisting of a film and a sheet. The material of the film or the sheet is not limited. For example, the film or the sheet may comprise a thermoplastic or thermosetting resin, a paper, a textile, a bonnet, a metal foil such as aluminum foil, and the like. For example, the film or sheet may be set on a heating rod, a heating bar or a heating plate which is covered by keratin fibers.

The coating means may comprise the heat energy source. Therefore, for example, the film or sheet which includes a heater may be set on a rod, a bar, or a plate which is covered by keratin fibers.

The occlusive conditions can restrict the evaporation of evaporable components such as water in the above-described composition applied to keratin fibers, and therefore the temperature of the keratin fibers can be increased higher than that obtainable by a conventional heating process or device for the keratin fibers in open conditions. Furthermore, the keratin fibers can be heated effectively, and the keratin fibers can be heated evenly.

According to one variation of the present invention, the occlusive space may comprise apertures, the surface area of which is less than 5%, preferably less than 3% and more particularly less than 0.5% of the total surface area of the coating means. According to this variation, the total surface area of the coating means comprises the surface area of, when it is present, an opening means for the coating means.

The apertures may be passages, holes or orifices, which may allow an exchange of air between the occlusive space and the exterior thereof, especially when the reaction such as forming vapor inside the occlusive space is too great. On the other hand, a person skilled in the art could form the apertures such that the diffusion of heat in the occlusive space is not impaired.

The keratin fibers are then heated. The heating process can be performed by any heating means which can be freely controlled to realize the temperature desired for the process. The keratin fibers can be heated at 50° C. to 250° C., preferably 60° C. to 200° C., more preferably 70° C. to 150° C., and even more preferably 80° C. to 100° C., during the step of heating the keratin fibers. The heating process may be performed for an appropriate time which is required to treat the keratin fibers. The time length for the heating process is not limited, but it may be from 1 minute to 2 hours, preferably 5 minutes to 1 hour, and more preferably 10 minutes to 40 minutes After the heating, the keratin fibers are optionally rinsed, and preferably dried.

According to the process of the present invention, no or very little reducing or oxidizing agent will be used to reshape or deform keratin fibers such as hair. Therefore, as compared to conventional reshaping or deforming processes for keratin fibers which require reducing/oxidizing of the keratin fibers, the process of the present invention can reduce the time required for reshaping or deforming the keratin fibers.

Furthermore, the process of the present invention uses no or very little reducing or oxidizing agent, and therefore, the damage to the keratin fibers can be reduced as compared to the conventional processes which require the use of the reducing or oxidizing agent.

EXAMPLES

The present invention will be described in a more detailed manner by way of examples. However, these examples should not be construed as limiting the scope of the present invention.

Examples 1 and 2 and Comparative Examples 1-3

The following compositions according to Examples 1 and 2 and Comparative Examples 1-3, shown in Table 1, were prepared by mixing the ingredients shown in Table 1. The numerical values for the amounts of the ingredients shown in Table 1 are all based on "% by weight" as active raw materials.

TABLE 1

|  | Ex. 1 | Comp. Ex. 1 | Comp. Ex. 2 | Ex. 2 | Comp. Ex. 3 |
| --- | --- | --- | --- | --- | --- |
| Histidine | 3 | 3 | 3 | — | — |
| Glycine | 10 | 10 | 10 | — | — |
| Arginine | — | — | — | 10 | 10 |
| pH adjuster | qs pH 9.5 | qs pH 7.5 | qs pH 9.5 | qs pH 10 | qs pH 10 |

TABLE 1-continued

|  | Ex. 1 | Comp. Ex. 1 | Comp. Ex. 2 | Ex. 2 | Comp. Ex. 3 |
| --- | --- | --- | --- | --- | --- |
| Hydroxypropyl guar | 0.8 | — | — | — | — |
| Hydroxyethylcellulose | — | — | — | 1 | — |
| Wave Intensity | +++ | + | ++ | +++ | ++ |
| Usability | +++ | − | − | +++ | − |

[Evaluation]

The compositions according to Examples 1 and 2 and Comparative Examples 1-3 were used for permanent waving of the hair.

Each of the compositions according to Examples 1 and 2 and Comparative Examples 1-3 in an amount of 1 g was applied to 1 g of a swatch of Chinese hair, the hair was wound around a perm roller with a diameter of 16 mm. The perm roller was then covered with a wrapping, and plugged on a digital perm machine. After heating at 90° C. for 25 minutes, the wrapping was removed, and the hair was cooled down. The perm roller was then removed, and the hair was rinsed off with water and dried.

The panelists evaluated the wave intensity and usability provided by the compositions according to Examples 1 and 2 and Comparative Examples 1-3 in accordance with the criteria shown below.

(Wave Intensity)

Wave intensity: the greater the number of curls formed, the stronger the wave intensity is.

The criteria of the evaluation were as follows.

+++: strong wave intensity

++: moderate wave intensity

+: poor wave intensity (Usability)

Usability: Dripping of the composition from the hair is evaluated.

The criteria of the evaluation were as follows.

+++: no dripping

++: very slight dripping

+: acceptable level of dripping

−: unacceptable level of dripping

The results of the evaluations are shown in Table 1.

The composition according to Example 1 has a pH of 9.5, and includes organic alkaline agents having a pKa value of from 8.0 to 13.5 ($pKa_2$ of histidine is 9.33, and $pKa_2$ of glycine is 9.78) and a polymeric thickener (hydroxypropyl guar). The composition according to Example 1 provides a strong wave intensity and no dripping from the hair is observed.

The composition according to Comparative Example 1 includes the same organic alkaline agents as Example 1, but it has a pH of 7.5, i.e., less than 8.0. The composition according to Comparative Example 1 provides much less wave intensity than Example 1 and an unacceptable level of dripping from the hair.

The composition according to Comparative Example 2 has a pH of 9.5, and includes the same organic alkaline agents as Example 1, but it does not include any polymeric thickener. The composition according to Comparative Example 2 provides less wave intensity than Example 1 and unacceptable level of dripping from the hair.

The comparison of the evaluation results for Example 1 and Comparative Examples 1 and 2 shows that the satisfaction of all the conditions of a pH of 8-12, the use of organic alkaline agent(s) having a pKa value of from 8.0 to 13.5, and the presence of a polymeric thickener is necessary to provide the target effects.

The composition according to Example 2 has a pH of 10.0, and includes another organic alkaline agent having a pKa value of from 8.0 to 13.5 (pKa$_2$ and pKa$_3$ of arginine is 8.99 and 12.48, respectively) and a polymeric thickener (hydroxyethylcellulose). The composition according to Example 2 provides a strong wave intensity and no dripping from the hair is observed.

The composition according to Comparative Example 3 has a pH of 10.0, and includes the same organic alkaline agent as Example 2, but it does not include any polymeric thickener. The composition according to Comparative Example 3 provides less wave intensity than Example 1 and unacceptable level of dripping from the hair.

The comparison of the evaluation results for Example 2 and Comparative Example 3 show that the satisfaction of all the conditions of a pH of 8-12, the use of organic alkaline agent(s) having a pKa value of from 8.0 to 13.5, and the presence of a polymeric thickener is necessary to provide the target effects.

The compositions according to Examples 1 and 2 satisfy all the requirements of a pH of 8-12, the use of organic alkaline agent(s) having a pKa value of from 8.0 to 13.5, and the presence of a polymeric thickener, and therefore, they can provide the target superior effects.

Examples 3-10 and Comparative Examples 4-7

The following compositions according to Examples 3-10 and Comparative Examples 4-7, shown in Table 2, were prepared by mixing the ingredients shown in Table 2. The numerical values for the amounts of the ingredients shown in Table 2 are all based on "% by weight" as active raw materials.

down. The perm roller was then removed, and the hair was rinsed off with water and dried.

The panelists evaluated the wave intensity and usability provided by the compositions according to Examples 3-10 and Comparative Examples 4-7 in accordance with the criteria shown below.

(Wave Intensity)

Wave intensity: the greater the number of curls formed, the stronger the wave intensity is.

The criteria of the evaluation were as follows.

+++: strong wave intensity
++: moderate wave intensity
+: poor wave intensity (Usability)

Usability: Both dripping of the composition from the hair and malodor were evaluated.

The criteria of the evaluation were as follows.

++: no dripping and no malodor
−: no dripping and malodor
−−: dripping and malodor The results of the evaluations are shown in Table 2.

The composition according to Example 3 has a pH of 10.0, and is free of ammonia or methionine, but includes an organic acidic agent having a pKa value of less than 3.5 (pK$_1$ of alanine is 2.35) and a polymeric thickener (xanthan gum). The composition according to Example 3 provides good cosmetic properties, good wave intensity and does not exhibit dripping and malodor.

The composition according to Comparative Example 4 has a pH of 10.0, and includes the same organic acidic agent as Example 3, whereas it also includes ammonia but it does not include a polymeric thickener, and therefore, the cos-

TABLE 2

|  | Ex. 3 | Comp. Ex. 4 | Comp. Ex. 5 | Ex. 4 | Comp. Ex. 6 | Comp. Ex. 7 | Ex. 5 | Ex. 6 | Ex. 7 | Ex. 8 | Ex. 9 | Ex. 10 |
|---|---|---|---|---|---|---|---|---|---|---|---|---|
| Alanine | 5 | 5 | 5 | – | – | – | – | – | – | – | – | – |
| Proline | – | – | – | 5 | 5 | 5 | – | – | – | – | – | – |
| Methionine | – | – | – | – | 2 | 2 | – | – | – | – | – | – |
| Glycine | – | – | – | – | – | – | 5 | – | – | 15 | – | – |
| CHES | – | – | – | – | – | – | – | 5 | – | – | 15 | – |
| Taurine | – | – | – | – | – | – | – | – | 5 | – | – | 15 |
| NH$_3$ | – | qs pH 10.0 | qs pH 10.0 | – | – | – | – | – | – | – | – | – |
| NaOH | qs pH 10.0 | – | – | qs pH 10.0 | qs pH 10.0 | qs pH 10.0 | qs pH 10.0 | qs pH 10.0 | qs pH 10.0 | qs pH 10.0 | qs pH 10.0 | qs pH 10.0 |
| Xanthan gum | 0.5 | – | 0.5 | – | – | – | – | – | – | – | – | – |
| HEC | – | – | – | 1 | – | 1 | – | – | – | – | – | – |
| Hydroxypropyl guar | – | – | – | – | – | – | 0.8 | 0.8 | 0.8 | 0.8 | 0.8 | 0.8 |
| Wave Intensity | ++ | + | ++ | ++ | + | ++ | ++ | ++ | ++ | +++ | +++ | +++ |
| Usability | ++ | −− | − | ++ | −− | − | ++ | ++ | ++ | ++ | ++ | ++ |

CHES: 2-(Cyclohexylamino)ethanesulfonic acid
HEC: Hydroxyethylcellulose

[Evaluation]

The compositions according to Examples 3-10 and Comparative Examples 4-7 were used for permanent waving of the hair.

Each of the compositions according to Examples 3-10 and Comparative Examples 4-7 in an amount of 1 g was applied to 1 g of a swatch of Chinese hair, the hair was wound around a perm roller with a diameter of 16 mm. The perm roller was then covered with a wrapping, and plugged into a digital perm machine. After heating at 90° C. for 25 minutes, the wrapping was removed, and the hair was cooled metic properties provided by the composition according to Comparative Example 4 are inferior to those provided by Example 3, and the wave intensity provided by the composition according to Comparative Example 4 is inferior to that provided by Example 3. In addition, the composition according to Comparative Example 4 exhibits dripping and malodor.

The composition according to Comparative Example 5 has a pH of 10.0, and includes the same organic acidic agent and polymeric thickener as Example 3, whereas it also includes ammonia, and therefore, the cosmetic properties provided by the composition according to Comparative Example 5 are inferior to those provided by Example 3, and the composition according to Comparative Example 5 exhibits malodor.

The comparison of the evaluation results for Example 3 and Comparative Examples 4 and 5 shows that both an organic acidic agent having a pKa value of less than 3.5 and a polymeric thickener, in a composition having a pH of from 8 to 12, are necessary to provide superior cosmetic effects and superior wave intensity, and that if ammonia is absent, more superior cosmetic effects can be provided.

The composition according to Example 4 has a pH of 10.0, and is free of ammonia or methionine, but includes another organic acidic agent having a pKa value of less than 3.5 ($pK_1$ of proline is 1.95) and a polymeric thickener (HEC). The composition according to Example 4 provides good cosmetic properties, good wave intensity and does not exhibit dripping and malodor.

The composition according to Comparative Example 6 has a pH of 10.0, and includes the same organic acidic agent as Example 4, and is free of ammonia, but includes methionine, whereas it does not include any polymeric thickener, and therefore, the cosmetic properties provided by the composition according to Comparative Example 6 are inferior to those provided by Example 4 and the wave intensity provided by the composition according to Comparative Example 6 is inferior to that provided by Example 4. In addition, the composition according to Comparative Example 6 exhibits dripping and malodor.

The composition according to Comparative Example 7 has a pH of 10.0, includes the same organic acidic agent and polymeric thickener as Example 4, and is free of ammonia, but includes methionine, and therefore, the cosmetic properties provided by the composition according to Comparative Example 7 are inferior to those provided by Example 4, and the composition according to Comparative Example 7 exhibits malodor.

The comparison of the evaluation results for Example 4 and Comparative Examples 6 and 7 shows that both an organic acidic agent having a pKa value of less than 3.5 and a polymeric thickener, in a composition having a pH of from 8 to 12, are necessary to provide superior cosmetic effects and superior wave intensity, and that if methionine is absent, more superior cosmetic effects can be provided.

The compositions according to Examples 5-10 have a pH of 10.0, are free of ammonia or methionine, and include an organic acidic agent having a pKa value of less than 3.5 and a polymeric thickener (hydroxypropylguar). The compositions according to Examples 5-10 provide good cosmetic properties, good wave intensity and do not exhibit dripping and malodor.

The compositions according to Examples 3-10 include an organic acidic agent having a pKa value of less than 3.5, and a polymeric thickener, and are free of ammonia or methionine, and therefore, they can provide superior cosmetic effects, good wave intensity and do not exhibit dripping and malodor.

The invention claimed is:

1. A method for providing keratin fibers with a wave or curl comprising:
    a) applying onto the keratin fibers a composition comprising:
        i. from 1 to 20% by weight, relative to the total weight of the composition, of at least one organic alkaline agent chosen from arginine, histidine, lysine, or mixtures of two or more thereof;
        ii. from 0.1 to 10% by weight, relative to the total weight of the composition, of at least one polymeric thickener; and
        iii. at least 50% by weight, relative to the total weight of the composition, of water;
    wherein the composition has a pH ranging from 9 to 11; and
    b) heating the keratin fibers at a temperature ranging from 50° C. to 250° C. for 1 minute to 2 hours; and
    c) optionally rinsing and/or drying the keratin fibers,
    wherein the method does not include application of reducing agents or oxidizing agents.

2. The method according to claim 1, wherein the hair is heated at a temperature ranging from 80° C. to 100° C. for about 10 minutes to about 40 minutes.

3. The method according to claim 1, wherein the keratin fibers are heated at a temperature of at least 80° C.

4. The method according to claim 1, wherein the composition further comprises at least one organic acidic agent.

5. The method according to claim 1, wherein the organic alkaline agent comprises arginine and/or histidine.

6. The method according to claim 5, wherein the polymeric thickener is chosen from cellulose, guar gum, xanthan gum, derivatives thereof, or mixtures of two or more thereof.

7. The method according to claim 6, wherein the total amount of the polymeric thickener ranges from 0.8 to 1% by weight, relative to the total weight of the composition.

8. The method according to claim 7, wherein the total amount of the organic alkaline agent ranges from 3 to 10% by weight, relative to the total weight of the composition.

9. A method for reshaping keratin fibers comprising:
    a) applying onto the keratin fibers a composition comprising:
        i. from 0.5 to 20% by weight, relative to the total weight of the composition, of at least one organic acidic agent chosen from glycine, taurine, alanine, proline, 2-(cyclohexylamino)ethanesulfonic acid, or mixtures of two or more thereof;
        ii. from 0.1 to 10% by weight, relative to the total weight of the composition, of at least one polymeric thickener;
        iii. at least one alkaline agent, and
        iv. at least 50% by weight, relative to the total weight of the composition, of water;
    wherein the composition has a pH ranging from 9 to 11; and
    wherein the composition is free of methionine;
    b) heating the keratin fibers at 50° C. to 250° C. for 1 minute to 2 hours; and
    c) optionally rinsing and/or drying the keratin fibers,
    wherein the method does not include application of reducing agents.

10. The method according to claim 9, wherein the at least one alkaline agent is an inorganic alkaline agent chosen from alkaline metal hydroxides, alkaline earth metal hydroxides, alkaline metal phosphates, alkaline metal monohydrogenophosphates, or mixtures of two or more thereof.

11. The method according to claim 9, wherein the at least one alkaline agent is present in an amount ranging from about 0.1% to about 20% by weight, relative to the total weight of the composition.

12. The method according to claim 9, wherein the hair is heated at a temperature ranging from 80° C. to 100° C. for about 10 minutes to about 40 minutes.

13. The method according to claim 9, wherein the polymeric thickener is chosen from cellulose, guar gum, xanthan gum, derivatives thereof, or mixtures of two or more thereof.

14. The method according to claim 13, wherein the total amount of the polymeric thickener ranges from 0.5 to 1% by weight, relative to the total weight of the composition.

15. The method according to claim 14, wherein the total amount of the organic acidic agent ranges from 5 to 15% by weight, relative to the total weight of the composition.

16. A method for providing keratin fibers with a wave or curl comprising:
a) applying onto the keratin fibers a composition comprising:
  i. from 2 to 15% by weight, relative to the total weight of the composition, of at least one agent chosen from arginine, histidine, lysine, glycine, taurine, alanine, proline, 2-(cyclohexylamino)ethanesulfonic acid, or mixtures of two or more thereof;
  ii. from 0.5 to 2% by weight, relative to the total weight of the composition, of at least one polymeric thickener chosen from cellulose, guar gum, xanthan gum, derivatives thereof, or mixtures of two or more thereof;
  iii. optionally at least one alkaline agent; and
  iv. at least 50% by weight, relative to the total weight of the composition, of water;
wherein the composition has a pH ranging from 9 to 11;
wherein the method does not include application of reducing agents or oxidizing agents;
b) heating the keratin fibers at a temperature ranging from 80° C. to 100° C.; and
c) optionally rinsing and/or drying the keratin fibers.

17. The method according to claim 16, wherein the composition comprises at least one alkalizing agent chosen from alkaline metal hydroxides, alkaline earth metal hydroxides, alkaline metal phosphates, alkaline metal monohydrogenophosphates, or mixtures of two or more thereof.

18. The method according to claim 16, comprising:
a) applying onto the keratin fibers a composition comprising:
  i. from 3 to 15% by weight, relative to the total weight of the composition, of at least one agent chosen from arginine, histidine, lysine, glycine, taurine, alanine, proline, 2-(cyclohexylamino)ethanesulfonic acid, or mixtures of two or more thereof;
  ii. from 0.5 to 1% by weight, relative to the total weight of the composition, of at least one polymeric thickener chosen from cellulose, guar gum, xanthan gum, derivatives thereof, or mixtures of two or more thereof;
  iii. optionally at least one alkaline agent chosen from alkaline metal hydroxides, alkaline earth metal hydroxides, alkaline metal phosphates, alkaline metal monohydrogenophosphates, or mixtures of two or more thereof; and
  iv. at least 50% by weight, relative to the total weight of the composition, of water;
wherein the composition has a pH ranging from 9.5 to 10;
b) heating the keratin fibers at a temperature ranging from 80° C. to 100° C. for about 10 minutes to about 40 minutes; and
c) rinsing and/or drying the keratin fibers.

* * * * *